(12) United States Patent
Nunes et al.

(10) Patent No.: US 8,127,459 B2
(45) Date of Patent: Mar. 6, 2012

(54) MULTIFUNCTIONAL AIRWAY EVALUATOR FOR OROTRACHEAL INTUBATION

(75) Inventors: Rogean R. Nunes, Fortaleza-Ceará (BR); Francisco Sergio Pinheiro Regadas, Forteleza-Ceará (BR); Steven D. Wexner, Parkland, FL (US)

(73) Assignee: Unique Surgical Innovations, LLC, Parkland, FL (US)

( * ) Notice: Subject to any disclaimer, the term of this patent is extended or adjusted under 35 U.S.C. 154(b) by 0 days.

(21) Appl. No.: 13/109,842

(22) Filed: May 17, 2011

(65) Prior Publication Data

US 2011/0214305 A1 Sep. 8, 2011

Related U.S. Application Data

(63) Continuation of application No. 12/703,429, filed on Feb. 10, 2010, now Pat. No. 7,954,251.

(60) Provisional application No. 61/202,297, filed on Feb. 17, 2009.

(51) Int. Cl.
*A61B 5/103* (2006.01)
(52) U.S. Cl. ............... 33/514; 33/807; 33/471; 600/590
(58) Field of Classification Search .................... 33/512, 33/807, 471; 600/590
See application file for complete search history.

(56) References Cited

U.S. PATENT DOCUMENTS

| | | | | |
|---|---|---|---|---|
| 1,969,052 A | * | 8/1934 | West | 33/376 |
| 3,266,156 A | * | 8/1966 | Debs | 33/424 |
| 4,404,752 A | * | 9/1983 | Hanna | 33/347 |
| 4,947,558 A | * | 8/1990 | Cummins | 33/797 |
| 4,955,141 A | * | 9/1990 | Welch | 33/418 |
| 5,154,003 A | * | 10/1992 | Moore | 33/558.01 |
| 5,507,098 A | * | 4/1996 | Schaver, Jr. | 33/371 |
| 7,600,325 B2 | * | 10/2009 | Zipplies | 33/514 |

* cited by examiner

*Primary Examiner* — Christopher Fulton
(74) *Attorney, Agent, or Firm* — Melvin K. Silverman; Yi Li

(57) ABSTRACT

A multifunctional airway evaluator for orotracheal intubation includes first and second connected elongated arms, movable relative to each other about a pivot axis, a planar plate connected to the first arm and extending upwardly therefrom, and a gravity-operated angular indicator attached to the planar plate. The plate includes a distance scale on its front face, and the distance scale includes a plurality of spaced apart grade lines aligned radially with the pivotal axis and distance parameters associated with the grade lines, each of the distance parameters indicating a distance between the distal ends of the first and second arms when the arms are in a relative position. The gravity-operated angular indicator includes an axial pin disposed perpendicular to the planar plate, a rotating disk pivotally attached to and rotatable around the axial pin by gravity, and one or more angular measurement marker provided adjacent the rotating disk.

19 Claims, 12 Drawing Sheets

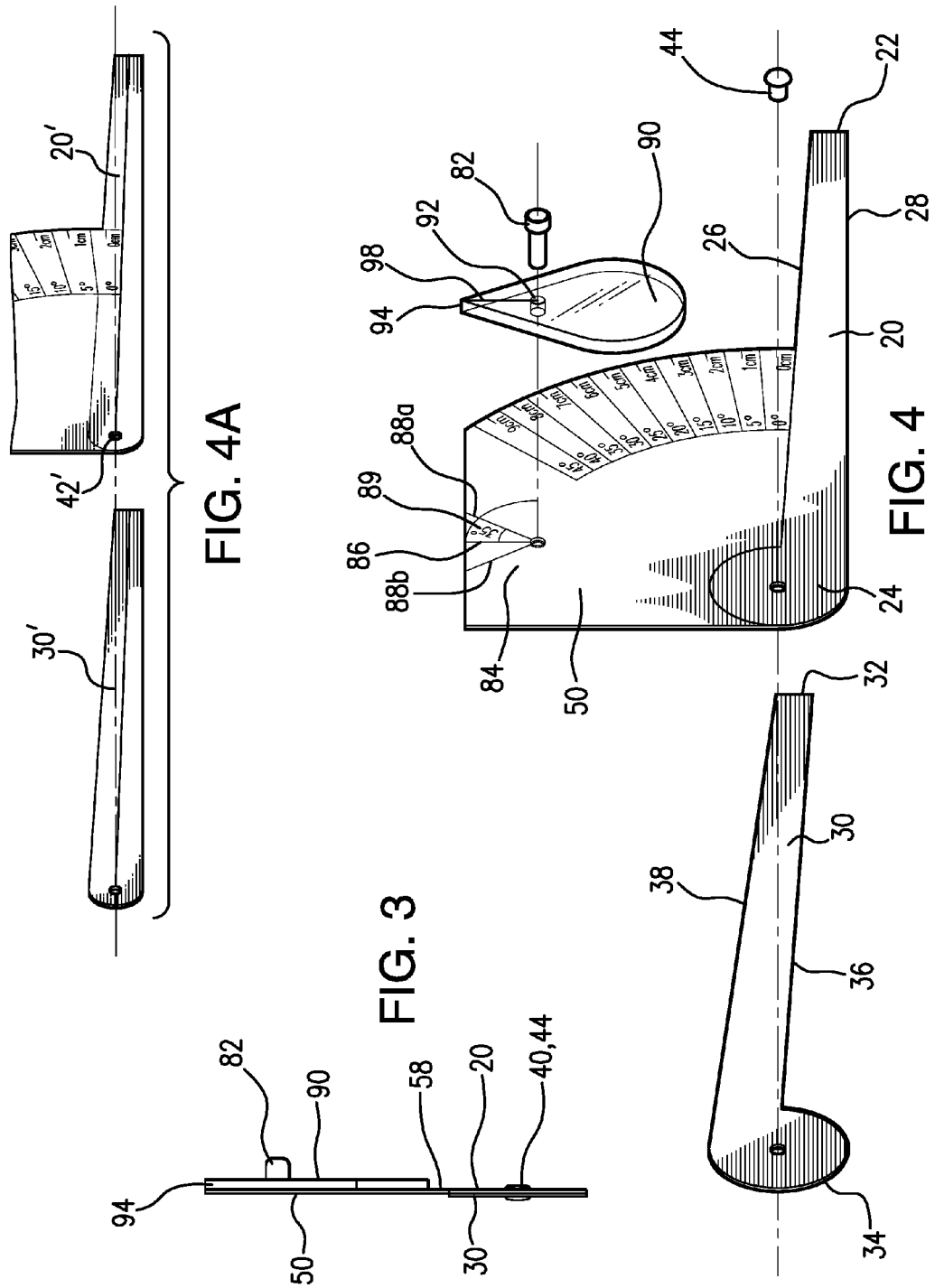

MULTIFUNCTIONAL AIRWAY EVALUATOR FOR OROTRACHEAL INTUBATION

CROSS REFERENCE TO RELATED APPLICATION

This application is a continuation of patent application Ser. No. 12/703,429, filed Feb. 10, 2010, now U.S. Pat. No. 7,954,251 B2, which claims the benefit under 35 USC 119(e) of provisional patent application Ser. No. 61/202,297, filed Feb. 17, 2009. Both parent applications are hereby incorporated by reference in their entirety.

FIELD OF THE INVENTION

The present invention relates to a device for evaluating airway for orotracheal intubation, more particularly relates to a multifunctional airway evaluator for orotracheal intubation and the method of use.

BACKGROUND OF THE INVENTION

Tracheal intubation is the placement of a flexible plastic tube into the trachea to protect the patient's airway and provide a means of mechanical ventilation. The most common tracheal intubation is orotracheal intubation where, with the assistance of a laryngoscope, an endrotracheal tube is passed through the mouth, larynx, and vocal cords, into the trachea. A bulb is then inflated near the distal tip of the tube to help secure it in place and protect the airway from blood, vomit, and secretions. Orotracheal intubation is often performed as needed in medical procedures by anaesthesiologists and other specialists, such as intensivists, pulmonologists, and emergency room doctors.

Maintenance of airway patency is a primary responsibility of anesthesiologists. Interruption of gas exchange, even for several minutes, can result in catastrophic outcomes such as brain damage or death. It has been reported that the vast majority (85%) of airway-related events involve brain damage or death, and as many as one third of deaths attributable solely to anesthesia have been related to inability to maintain a patent airway. The difficulty of achieving a patent airway varies with anatomic and other individual patient factors, and identification of the patient with a difficult airway is vital in planning anesthetic management so that orotracheal intubation and positive pressure ventilation can be achieved safely. Several clinical criteria can be routinely assessed on patients prior to anesthesia including mouth opening distance, Mallampati classification, neck mobility, ability to prognath, thyromental distance, body weight, and previous history of difficult intubation.

Accurate preoperative prediction of potential difficulty with intubation can help reduce the incidence of catastrophic complications by alerting anesthesia personnel to take additional precautions before beginning anesthesia and establishing an artificial airway. In addition, more accurate prediction of difficulty with intubation can potentially reduce the frequency of unnecessary maneuvers (for instance, awake intubation) related to false positive predictions.

Several evaluation criteria have been proposed. Recently, Janssens et al have proposed a quantitative evaluation approach using airway difficulty score (ADS) as shown in the table below. Airway Difficulty Score represent the sum of the points for five criteria of difficult intubation. As shown, the total score can vary from 5 to 15, and if score is higher or equal to 8, ventilation and/or intubation are considered likely to be difficult.

| Airway Difficulty Score (ADS) | | | |
|---|---|---|---|
| Score | 1 | 2 | 3 |
| Thyromental distance | >6 cm | 5-6 cm | <5 cm |
| Mallampati class | Class I | Class II | Class III & IV |
| Mouth opening | 4 cm | 2-3 cm | 1 cm |
| Neck mobility | Normal (≧35°) | Reduced | Fixed flexion |
| Upper incisors | Absent | Normal | Prominent |

If score ≧8, ventilation and/or intubation likely to be difficult (Janssens et al., European Journal of Anaesthesiology, 2001, 18, 3-12)

In addition to the above five parameter, mandibular angle distance has also been considered important in evaluation of airway. Among these tests, Mallampati class and upper incisors can be examined by visual observation. However, determination of mouth opening distance, thyromental distance, mandibular angle distance, and neck mobility of a patient requires using measurement equipments.

Currently, limited tools are available for making the above described distance and angular measurements. Doctors use ruler, measuring tape, paquimeter, and also commonly use their fingers or hands, to make the distance measurements. Moreover, there is no specific device available for clinical measurement of the neck mobility angle. This renders the measurements difficult and less accurate, considering the subject of the measurements and unnatural positions that the patient is in. Lack of accuracy in the measurements may result in life threatening consequences, for example when a false negative is reported from the measurements.

Furthermore, for distance and angular measurements at least two different measuring devices are used. As such, doctors need to carry, or have access to, more than one device for the required measurements. On the other hand, considering the subject and environment of the measurements, the devices used should be either disposable or can be sterilized if they are intended to be used repetitively. It is costly to supply and maintain multiple disposable measurement devices.

Therefore, there exists a strong need for a measurement device that is designated and particularly suitable for providing accurate airway evaluation for orotracheal intubation, and an integrated measurement device that can be used for both distance and angular measurements for airway evaluation. It is further desirable to have a low cost disposable device that can be conveniently carried by doctors or made readily available in medical facilities.

SUMMARY OF THE INVENTION

In one aspect, the present invention is directed to a multifunctional airway evaluator for orotracheal intubation. In one embodiment, the multifunctional airway evaluator comprises a first elongated arm having a distal end and an opposing hinge end; a second elongated arm having a distal end and an opposing hinge end connected to the hinge end of the first arm by a pivot connection, the first and second arms movable relative to each other about a pivotal axis of the pivot connection; a planar plate connected to the first arm and extending upwardly from an upper edge of the first arm, between the hinge end and a middle portion of the first arm, and a gravity-operated angular indicator attached to the planar plate. The plate includes a distance scale on a front face of the planar plate, and the distance scale includes a plurality of spaced apart grade lines, each thereof aligned radially with the pivotal axis, and distance parameters associated with the grade lines, each of the distance parameters indicating a distance between the distal ends of the first and second arms when the arms are in a relative position. The gravity-operated angular indicator includes an axial pin disposed perpendicular to the planar plate, a rotating disk pivotally attached to and rotatable around the axial pin by gravity, and one or more angular measurement marker affixed adjacent the rotating disk.

In one embodiment, the gravity-operated angular indicator further includes a base fastened to the planar plate. The axial pin and the rotating disk are attached to the base, and the angular measurement marker is placed on a front surface of the base. The base has a shape of a clip and is slid onto an upper portion of the planar plate.

In a further aspect, the present invention is directed to a method of evaluation of airway for orotracheal intubation. The method comprises providing a multifunctional airway evaluator described above, placing the distal ends of the first and second arms next to a first and a second predetermined locations of the body of a patient, respectively, and recording a measured distance between the first and second predetermined locations from the distance scale; and affixing the planar plate at a third predetermined location of the body of the patient, with a vertical central axis of the rotating disk aligned with a zero-degree reference line of the gravity-operated angular indicator, and then instructing the patient to carry out a flexion movement involving tilting of the third location of the body, and recording an extent of rotation of the rotating disk from the angular measurement marker of the gravity-operated angular indicator.

In one embodiment, the first and second predetermined locations of the body are mandibular and maxillary central incisors, respectively, while the mouth of the patient is fully opened, and the measured distance is mouth opening distance of the patient. In another embodiment, the first and second predetermined locations of the body are the thyroid notch and bone point of the mentum of the mandible of the patient, respectively, while the neck of the patient is in full extension, and the measured distance is thyromental distance of the patient. In a further embodiment, the first and second predetermined locations of the body are the left mandibular angle and the right mandibular angle of the patient, respectively, and the measured distance is mandibular angle distance of the patient.

In yet another embodiment the third predetermined location is the pre-auricular area of the patient, and the flexion movement is tilting of the head of the patient upwardly to a maximum extent while maintaining cervical spine in a neutral position, and the extent of rotation of the rotating disk represents neck mobility of the patient.

The advantages of the present invention will become apparent from the following description taken in conjunction with the accompanying drawings showing exemplary embodiments of the invention.

BRIEF DESCRIPTION OF THE DRAWINGS

FIG. 3 is a side view of the airway evaluator shown in FIG. 1.

FIG. 4 is an exploded view of the airway evaluator shown in FIG. 1. FIG. 4A is a partial view of an alternative embodiment of the airway evaluator shown in FIGS. 1 and 4, with the central axes of the two arms aligned with the pivot axis.

It is noted that in the drawings like numerals refer to like components.

DETAILED DESCRIPTION OF THE INVENTION

Figure 1:
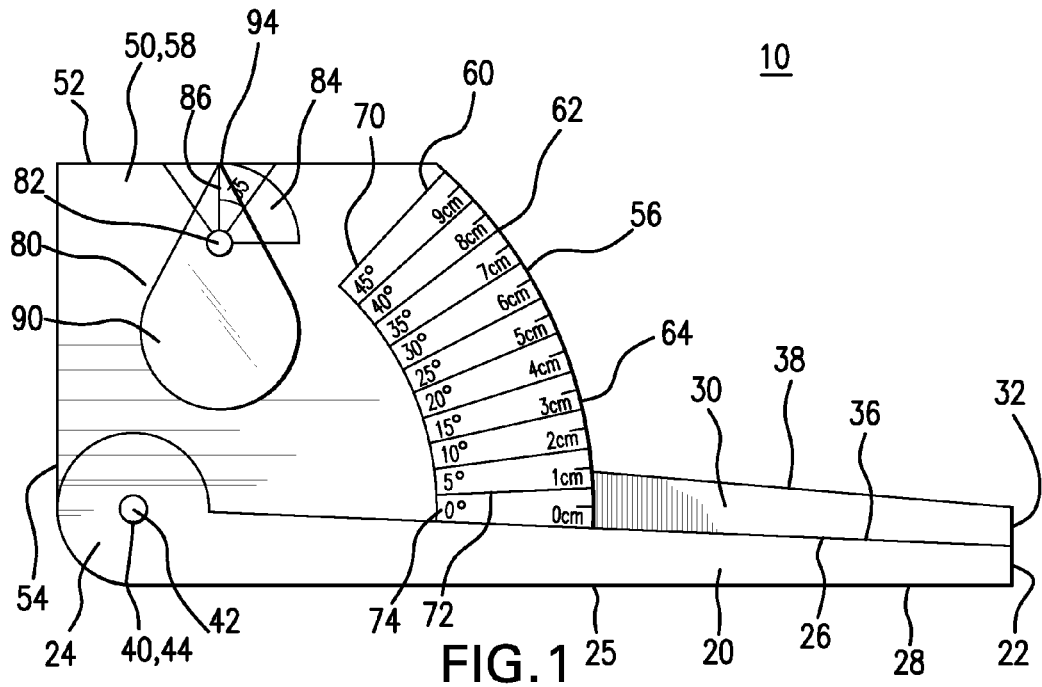
FIG. 1 is a front view of the airway evaluator in one embodiment of the present invention, with the first and second arms in a horizontal and relatively closed position.
Figure 2:
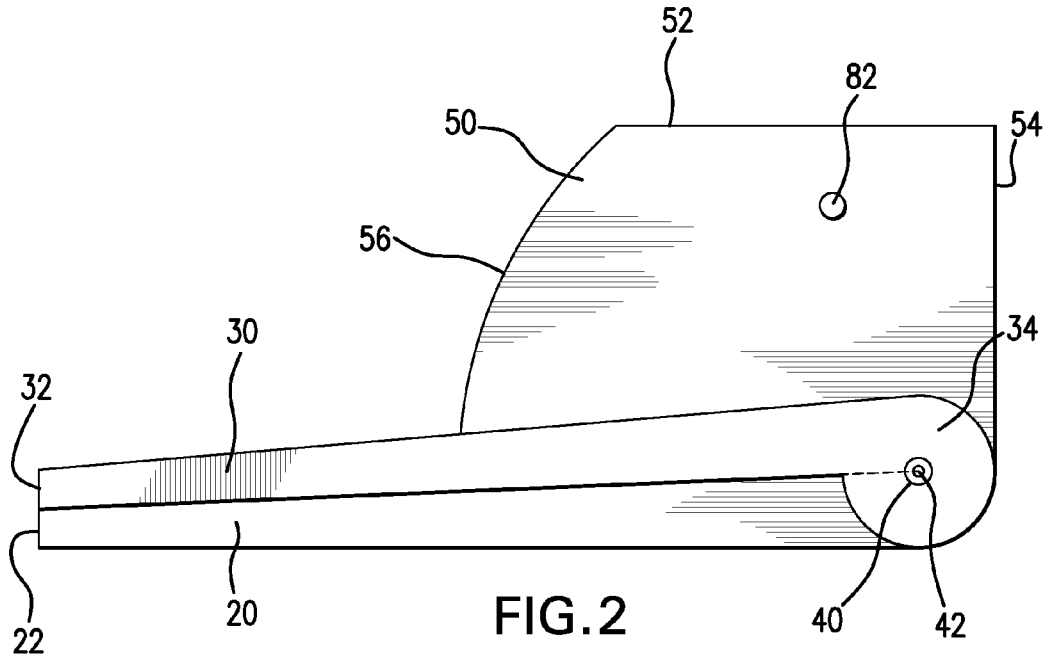
FIG. 2 is a rear view of the airway evaluator at the position shown in FIG. 1, wherein the dotted line is merely provided to show the alignment of the two arms with the pivotal axis.
Figure 5A:
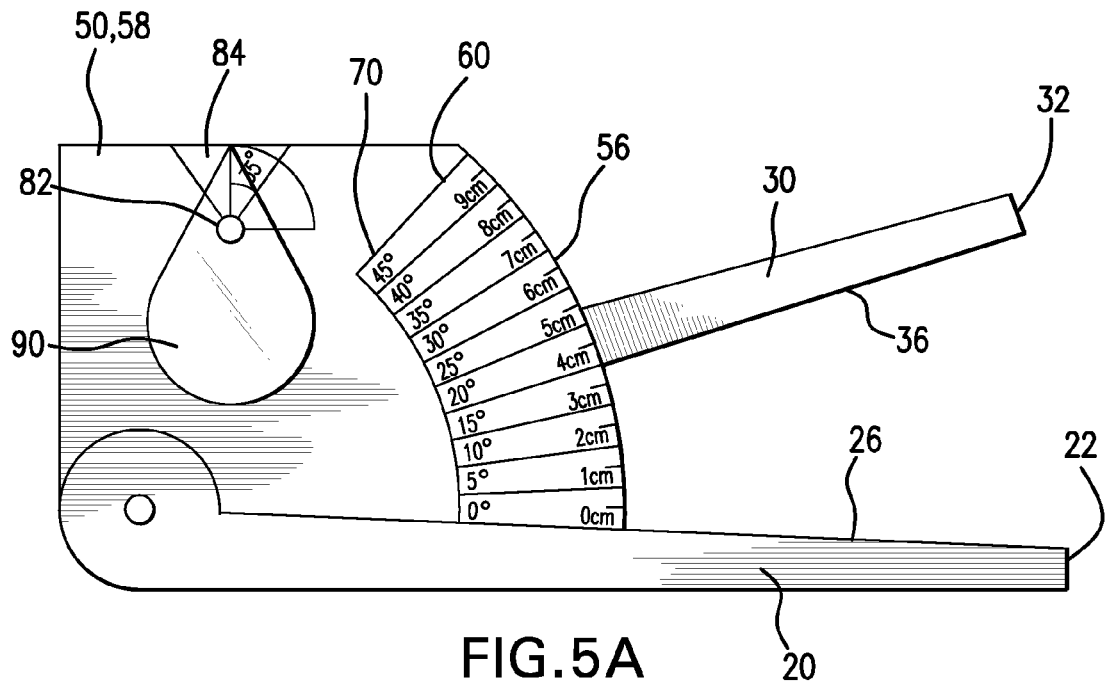
FIGS. 5A and 5B are front and rear views of the airway evaluator shown in FIG. 1, with the second arm rotated away from the first arm, as when the device is used for measurement.
Figure 5B:
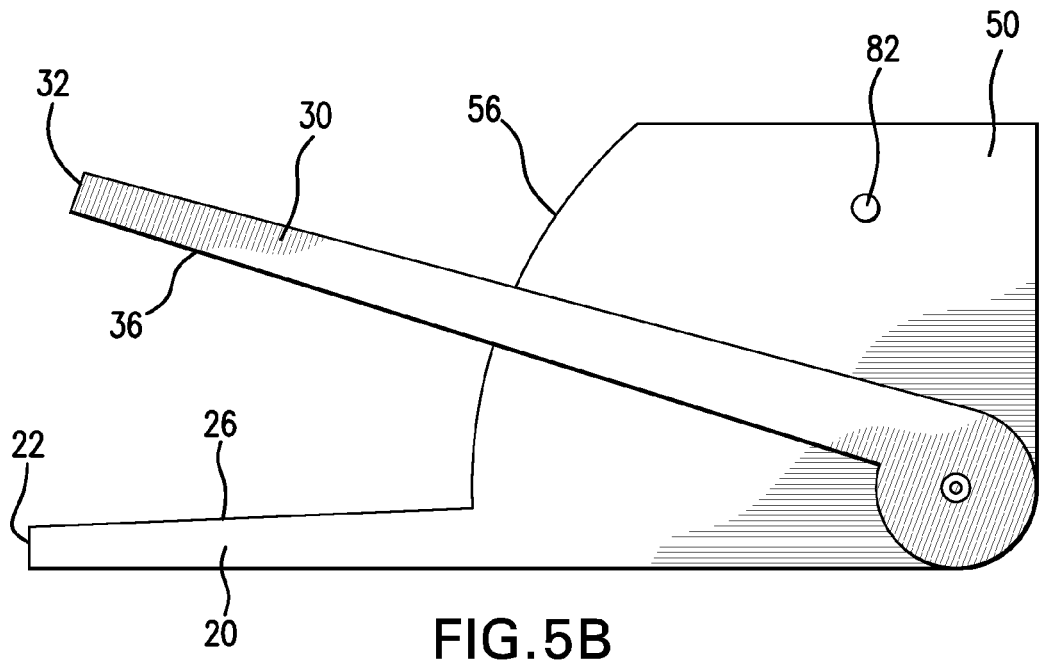

In one aspect, the present invention provides a multifunctional airway evaluator for orotracheal intubation.

Referring now to FIGS. 1-7, in one embodiment a multifunctional airway evaluator 10 comprises a first elongated arm 20, a second elongated arm 30, a planar plate 50 and a gravity-operated angular indicator 80.

As shown, the first elongated arm 20 has a distal end 22, an opposing hinge end 24, an inner edge 26 and an outer edge 28. The second elongated arm 30 has a distal end 32, an opposing hinge end 34, an inner edge 36, and an outer edge 38, see FIGS. 1 and 5A. The hinge ends 24 and 34 of first and second arms are connected together by a pivot connection 40. The first and second arms are movable relative to each other about a pivotal axis 42 of pivot connection 40. The pivot connection can be effected by pivot pins, pivot screws or other suitable means. In the embodiment shown, hinge ends 24 and 34 of the two arms are connected by a headed pivot pin 44.

Preferably, the first and second arms are linear and have the same length. The length of the first and second arms can be from about 9 centimeter (cm) to about 18 cm, preferably from about 10 cm to about 14 cm. Optionally, the two arms can be slightly tapered from their hinged ends toward the distal ends. Preferably, hinge ends 24 and 34 of the first and second arms are enlarged, and inner edge 36 of second arm 30 and inner edge 26 of first arm 20 are aligned with pivotal axis 42, as shown FIGS. 1-2 and 5-6. The advantages of such an alignment can be better understood in reference to the operating mechanism of the airway evaluator and the method of use described in more detail hereinafter. In the embodiment shown, second arm 30 is disposed on a rear side of first arm 20 behind planar plate 50. However, second arm 30 can also be disposed on the front side of first arm 20, particularly when the second arm is made of a transparent material, which will not obstruct the scales on plate 50.

Planar plate 50 is disposed between hinge end 24 and about the middle portion 25 of first arm 20, and extends upwardly from inner edge 26 of first arm 20. Planar plate 50 is affixed to first arm 20. In the embodiment shown, planar plate 50 and first arm 20 are made of one integral piece of material, as such the first arm is stationary. However, planar plate 50 can also be a separate element, affixed to first arm 20 by fasten means such as adhesive, screws, or pins. The plate and the first and second arms can be made of a thin plate solid material, including but not limited to, postcard paper, three-ply paper or triplex paper, plastics, wood, and metal. Moreover, plate 50 can be made of a same or different material from the material of the two arms. In one exemplary embodiment, the plate and both arms are made of a triplex paper having a thickness of 1 mm and a density of 28 g/m$^2$.

As shown in FIG. 1, plate 50 has an upper edge 52, a first side edge 54 on the hinge end 24 of first arm 20, and an opposing second side edge 56 about the middle portion 25 of first arm 20. Herein, middle portion 25 of first arm 20 refers to a portion of the first arm from about one fourth to about three fourth of its length from the hinge end. In other words, the position of second side edge 56, or the width of plate 50 can vary substantially. In one exemplary embodiment, first and second arms 20 and 30 have a length about 12.8 centimeter (cm), and the width of plate 50, between first side edge 54 and the merging point of second side edge 56 with the first arm, is about 7 cm. Preferably, second side edge 56 is circularly curved relative to pivot axis 42. However, the second side edge can also have other shapes, for example, vertical or tapered.

As shown, plate 50 includes a distance scale 60 on front face 58 of the plate. Distance scale 60 includes a plurality of spaced apart grade lines 62 and distance parameters 64 associated with grade lines 62. Each grade line 62 is aligned radially with pivotal axis 42. Each distance parameter indicates a corresponding distance between distal end 22 of first arm 20 and distal end 32 of second arm 30, when the two arms are in a position relative to each other. Distance scale 60 is disposed circularly relative to pivot axis 42. Preferably, distance scale 60 is disposed along the circularly curved second side edge 56, which eases reading of the measured distance parameter associated with the grade line with which the second arm 30 aligns. However, as can be appreciated when plate 50 is made of a transparent material, the position of second arm 30 relative to distance scale 60 can be clearly recognized without the aid of circular side edge 56.

The distance parameters can be expressed by metric or English units, preferably by metric units, since subject measurements to be made by the airway evaluator are commonly expressed by metric units in medical examinations. Resolution of the distance scale 60 can be from 0.1 to 1 cm, preferably about 0.5 cm.

Figure 6:
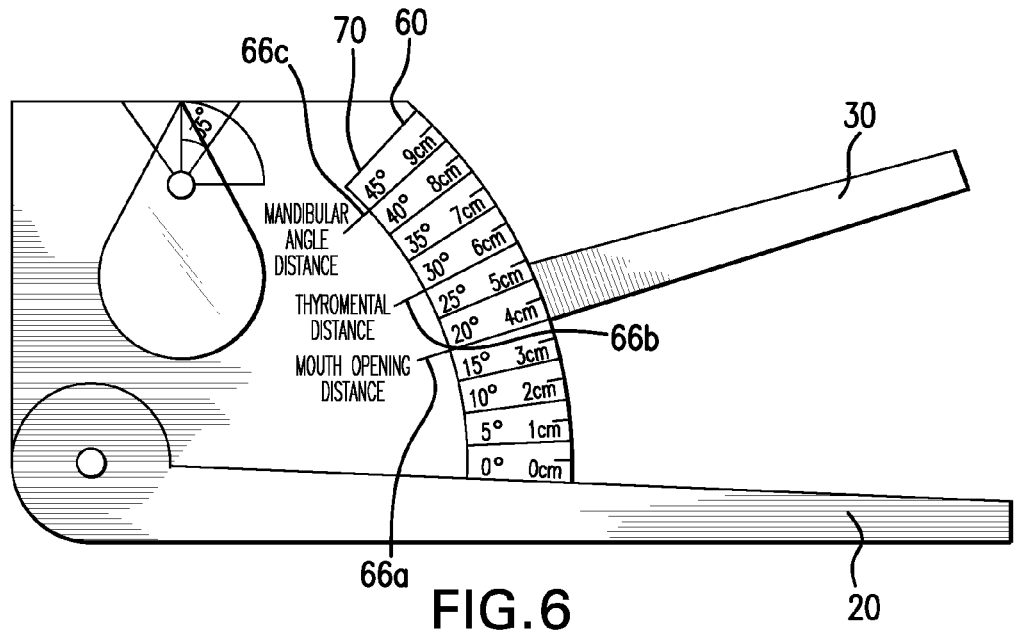
FIG. 6 is a front view of a further embodiment of the airway evaluator shown in FIG. 1, which includes threshold markers for evaluation of airway.

In a further embodiment as shown in FIG. 6, optionally distance scale 60 further includes one or more threshold markers, indicating one or more predetermined threshold distances. As shown, threshold marker 66a indicates a recommended threshold mouth opening distance, and threshold marker 66b indicates a recommended threshold thyromental distance, and threshold marker 66c indicates a recommended threshold mandibular angle distance for orotracheal intubation. Moreover, threshold markers can be further highlighted for easy recognition of clinically recommended thresholds.

Figure 8:
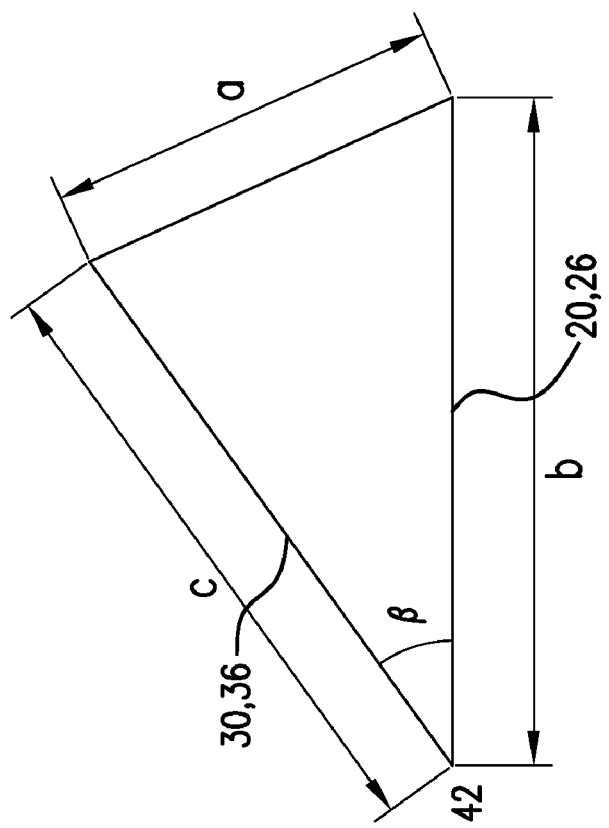
FIG. 8 is an illustrative view showing the mechanism of the distance scale of the airway evaluator.

The operating mechanism of distance scale 60 can be understood in reference to FIG. 8. The geometrical relationship of the distance between first arm 20 and second arm 30 can be expressed by the following equation:

$$a^2 = b^2 + c^2 - 2ab \cdot \cos(\beta)$$

where "a" is the distance between distal end 22 of first arm 20 and distal end 32 of second arm 30, "b" is the length of first arm 20, "c" is the length of second arm 30, and β is the angle between the two arms.

As can be appreciated, the distance scale 60 depends on, or varies with, the length of the arms. In one exemplary embodiment, the length of the arms is about 11.6 cm from the distal ends to pivot axis 42. On the other hand, as can be further appreciated in FIG. 8, distance "a" is measured between the two lines that are in alignment with pivot axis 42. In the exemplary embodiment shown in FIG. 1 and also illustrated in FIG. 8, the inner edge 26 of first arm 20 and the inner edge 36 of second arm 30 are in alignment with pivot axis 42. As such, distance "a" as measured using airway evaluator 10 shown in FIG. 1 is the distance between the inner edges 26 and 36 of the first and second arms. As shown in FIG. 1, distance scale 60 starts from the inner edge 26 of first arm 20, in other words, the zero point of distance scale 60 is in line with the inner edge 26 of first arm 20. A measured distance is read at the position with which the inner edge 36 of second arm 30 is aligned. However, it should be understood that other planes along the longitudinal axis of the first and second arms can also be aligned with the pivot axis of the device and the reading of a measurement can be made at a corresponding position along the edge of the distal end accordingly. For example, as illustrated as an alternative embodiment in FIG. 4A, if the pivot axis 42' is in alignment with the central axes of both the first and the second arms 20', 30', instead of in alignment with the inner edge 26 and the inner edge 36 as shown in the embodiment shown in FIG. 1, then distance "a" between the two arms is the distance between the central axes of the two arms at their distal ends. With this configuration, indicator lines along the central axes of the two arms, respectively, may be provided to assist the measurement.

Optionally, plate 50 may further include an angular scale 70 disposed aside distance scale 60. The angular scale 70 includes a plurality of spaced apart grade lines 72 and angular parameters 74 associated with grade lines 72. Each grade line 72 is aligned radially with pivotal axis 42. Each angular parameter indicates an angle between first arm 20 and second arm 30. In the exemplary embodiment shown, grade lines 72 of angular scale 70 are coincide with grade lines 62 of distance scale 60. However, grade lines 72 of angular scale 70 can be separate and different from the positions of grade lines 62 of distance scale 60, for example, when the angular parameters have a resolution larger or smaller than that shown in the exemplary embodiment.

The gravity-operated angular indicator 80 is attached to planar plate 50, preferably at an upper portion thereof. Gravity-operated angular indicator 80 includes an axial pin 82 disposed perpendicular to planar plate 50, a rotating disk 90 pivotally attached to and rotatable around axial pin 82 by gravity, and one or more angular measurement markers 84 affixed adjacent rotating disk 90.

Axial pin 82 can be made of metal or other suitable materials, preferably with a smooth exterior surface. Rotating disk 90 has an aperture 92, through which axial pin 82 is inserted (see FIG. 4). Aperture 92 has an inner diameter larger than the outer diameter of axial pin 82, as such disk 90 can rotate freely around the axial pin. Preferably, rotating disk 90 has a centered pointed upper end 94. The pointed upper end 94 helps the reading of measured angles. In the embodiment shown, rotating disk 90 has a general tear drop shape with a pointed upper end 94. However, other suitable shapes, such as an elongated triangle or rectangle, can also be used. Rotating disk 90 can be made of plastics, metal or other suitable materials. It is advantageous that the rotating disk is made of a transparent material, because angular measurement markers behind the rotating disk can be clearly visualized. Optionally, rotating disk 90 further includes a pointer line 98 marked on the front surface of the disk downwardly from pointed upper end 94 along the vertical central axis of the rotating disk. Pointer line 98 helps reading of the measured angle, particularly when the rotating disk is transparent.

Figure 7:
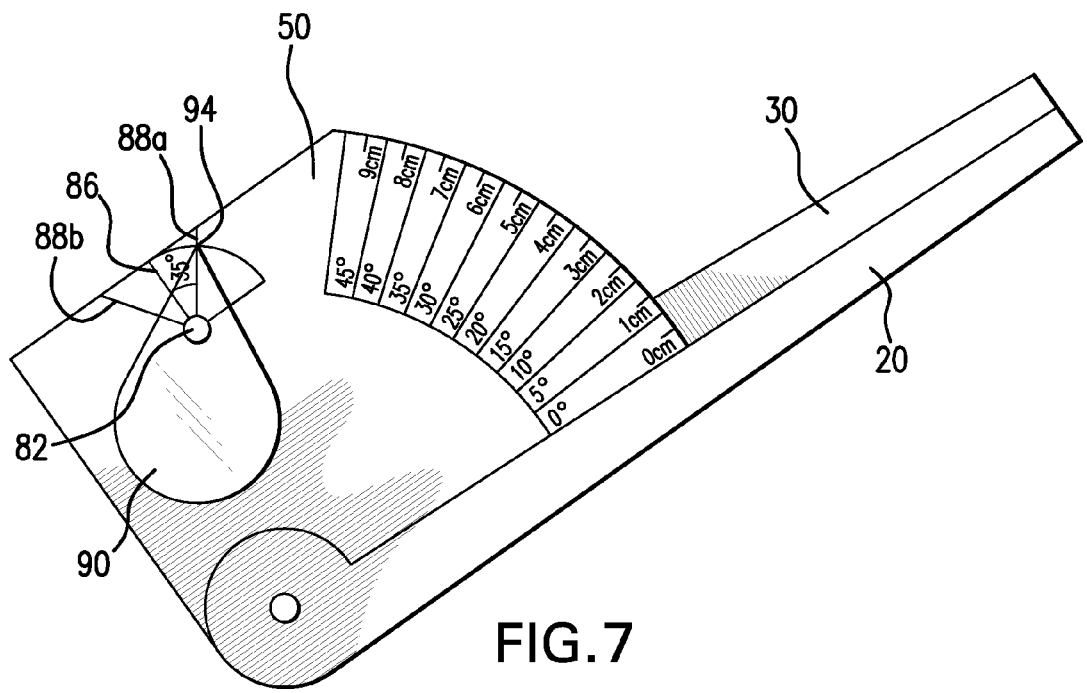
FIG. 7 is a front view of the airway evaluator shown in FIG. 1, with the planar plate tilted 35 degree from the horizontal position.
Figure 9:
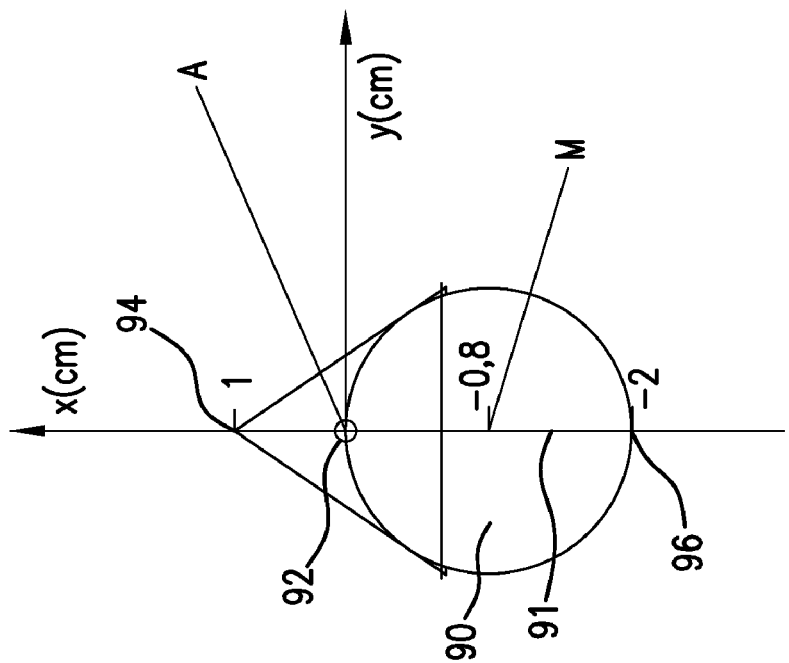
FIG. 9 is an illustrative view showing the geometric relationship of the gravity-operated angular indicator.

The mass center of rotating disk 90 is distanced from axial pin 82 or the axis of rotation of the rotating disk. In the exemplary embodiment shown in FIG. 1, rotating disk 90 is attached to axial pin 82 at one third of its length from the upper end 94, along vertical central axis 91 of the rotating disk (see FIG. 9). The geometric relationship of rotating disk 90 is further illustrated in FIG. 9. As shown, in a Cartesian plane with the axis of rotation (A) as the origin and the vertical central axis 91 of the rotating disk aligned with x-axis, the mass center (M) has a coordinate of x=−0.8 and y=0, the upper end 94 has a coordinate of x=1 and y=0, and the lower end 96 of the disk has a coordinate of x=−2 and y=0. As can be appreciated, the rotational movement of rotating disk 90 is induced by gravity. When planar plate 50 is tilted from a horizontal position as shown in FIG. 7, rotating disk 90 rotates around axial pin 82 and always repositions its vertical central axis 91 to the vertical position.

As shown in FIGS. 1 and 4, angular measurement markers 84 are provided on front face 58 of planar plate 50 next to the upper portion of rotating disk 90. The angular measurement markers can be provided by printing, painting, or embossing. Angular measurement markers 84 include a zero-degree reference line 86, one or more assessment lines, 88*a*, 88*b*, aligned radially with axial pin 82, and one or more angular parameters 89 associated with the assessment lines (see FIG. 4). The zero-degree reference line and the assessment lines are stationary. Zero-degree reference line 86 is used to indicate a starting position of a rotational movement of rotating disk 90. In the embodiment shown, a zero-degree reference line 86 is also a vertical reference line. Since rotating disk 90 is always in the vertical position, when the gravity-operated angular indicator 80 is in its vertical position, vertical central axis 91 of the rotating disk is in alignment with the zero-degree reference line 86, and the pointed upper end 94 of the rotating disk points to zero-degree reference line 86. This typically is the starting position of a measurement as further described hereinafter in reference to the method of use.

However, the zero-degree reference line may also assume other suitable orientations, for example as a horizontal reference line. With this configuration, rotating disk further includes a horizontal indicator line that is perpendicular to vertical central axis 91 of the disk shown in FIG. 9. In this case, when the stationary horizontal reference line is in line with the horizontal indicator line on the rotating disk, it indicates a starting position of a rotational movement of the disk.

Assessment lines 88*a*, 88*b* represent at least one predetermined threshold angle that is numerically expressed by the angular parameter. In the embodiment shown, assessment lines 88*a*, 88*b* indicate a 35 degree angle from the zero-degree reference line 86. Since assessment lines 88*a*, 88*b* are aligned radially with axial pin 82 or axis of rotation of rotating disk 90, the extent of rotation of rotating disk 90 can be determined according to the assessment lines. The presence of assessment lines 88*a* and 88*b* on both sides of the zero-degree reference line 86 provides flexibility in using the airway evaluator for angular measurement, as an angular measurement can be made in either direction.

As can be understood, the operation of gravity-operated angular indicator 80 is induced by gravity, therefore, its operation is independent of the operation of the arms of the airway evaluator.

Figure 10:
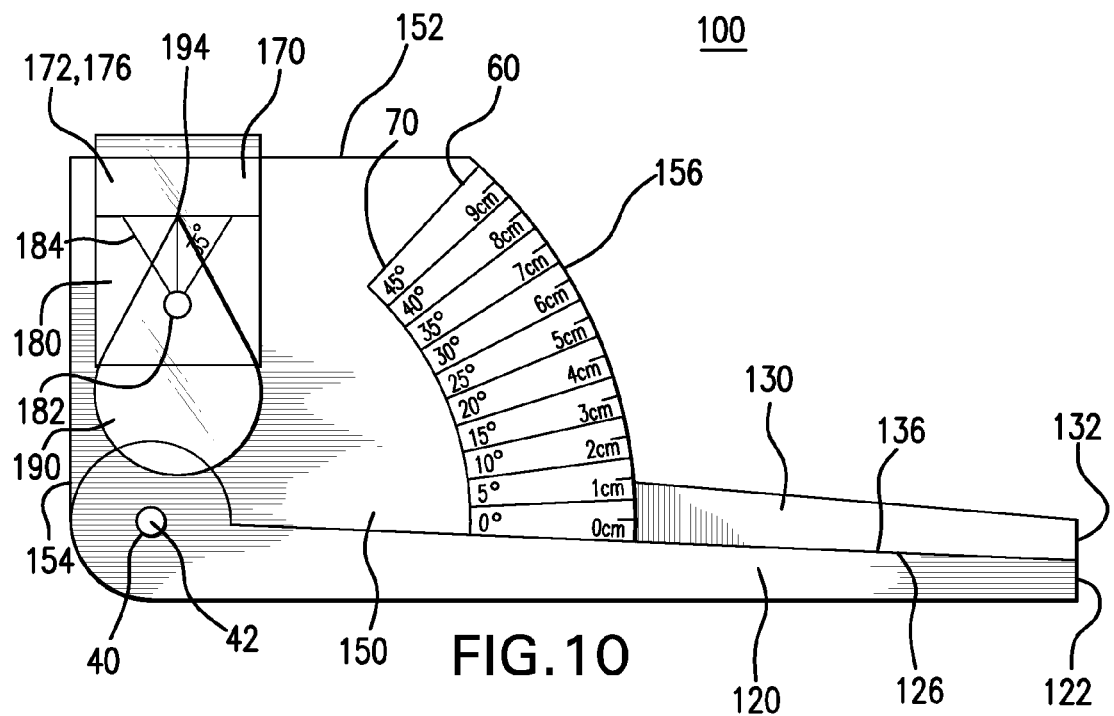
FIG. 10 is a front view of the airway evaluator in a further embodiment of the present invention, in which the gravity-operated angular indicator is removable from the planar plate.
Figure 11:
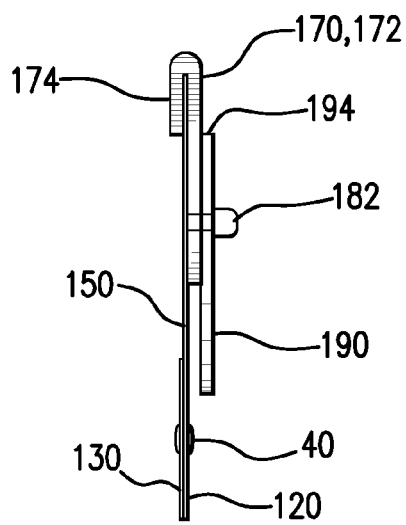
FIG. 11 is a side view of the airway evaluator shown in FIG. 10.
Figure 12:
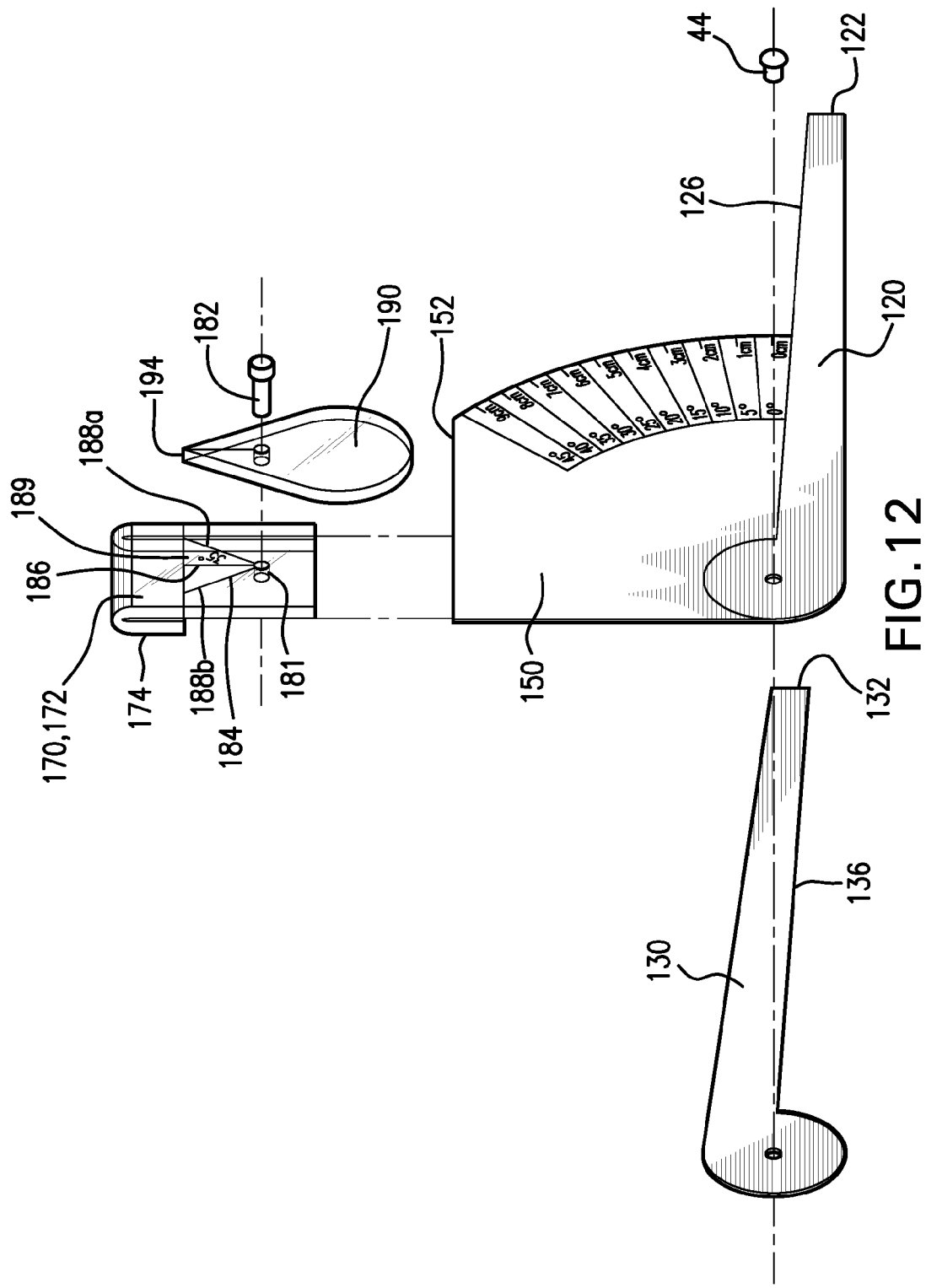
FIG. 12 is an exploded view of the gravity-operated angular indicator shown in FIG. 10.

FIGS. 10-12 illustrate a further embodiment of the multifunctional airway evaluator of the present invention. As shown in FIG. 10, multifunctional airway evaluator 100 comprises a first elongated arm 120, a second elongated arm 130, a planar plate 150 and a gravity-operated angular indicator 180. The structures and operation mechanism of first and second arms 120 and 130 are the same as those of the first and second arms 20 and 30 of airway evaluator 10 described above. The structure of planar plate 150 is the same as that of plate 50 of airway evaluator 10 described above, which includes the above described distance scale 60 and optionally angular scale 70 along a second side edge 156.

Airway evaluator 100 includes a removable gravity-operated angular indicator 180 fastened on planar plate 150. As more clearly shown in FIG. 12, gravity-operated angular indicator 180 includes a base 170, an axial pin 182 affixed perpendicularly to base 170, a rotating disk 190 pivotally attached to and rotatable around axial pin 182 by gravity, and one or more angular measurement markers 184 affixed on base 170 adjacent the upper portion of rotating disk 190.

As shown in FIGS. 11 and 12, base 170 has a shape of clip, with a front panel 172 and a rear portion 174. The distance between front panel 172 and rear portion 174 is sufficient to tightly insert planar plate 150. Axial pin 182 and rotating disk 190 are disposed on the front side of front panel 172. Angular measurement markers 184 are printed on the front surface of front panel 172. Base 170 is slid onto the upper edge 152 of planar plate 150 and stays stationary as shown in FIG. 10. In one exemplary embodiment, base 170 has a height about 2.6 cm and a width about 2 cm, and axial pin 182 is affixed about 1.3 cm from the top of base 170. Base 170 can be made of plastics, metals or other suitable materials. In one exemplary embodiment, both base 170 and rotating disk 190 are made of a transparent thermoplastic, for example synthetic polymer of methyl methacrylate.

The structure of rotating disk 190 is the same as that of rotating disk 90 described above. Similar to angular measurement markers 84 described above, angular measurement markers 184 include a zero-degree or vertical reference line 186, one or more assessment lines, 188*a*, 188*b*, aligned radially with axial pin 182, and one or more angular parameters 189 associated with the assessment lines. Angular measurement markers 184 are provided on the front surface of front panel 172, behind the upper portion of rotating disk 190. In the embodiment shown, zero-degree reference line 186 and assessment lines, 188*a*, 188*b*, radially extend from aperture 181 in which axial pin 182 is inserted. This clearly shows axial pin 182 as the axis of rotation of rotating disk 190.

The operation mechanism of gravity-operated angular indicator 180 is the same as that of the angular indicator 80 described above. It is noted that in the embodiment shown in FIG. 10, base 170 is fastened on the upper edge 152 of planar plate 150, with rotating disk 190 disposed at the front side of plate 150. However, when needed the direction of base 170 can be reversed, namely with rotating disk 190 disposed at the rear side of plate 150. Moreover, base 170 may also be fastened on first side edge 154. In this case, the zero-degree reference line and assessment lines may be rotated 90 degrees from those shown in FIG. 10, and alternatively, when in use the airway evaluator can also be positioned 90 degrees clockwise from that shown in FIG. 16A.

As can be appreciated, the airway evaluator of the present invention is small in size, and it can be conveniently carried by the doctors in their pockets. The airway evaluator can be either made as a disposable device for one time use, or made as a reusable device. As a disposable device, the planar plate is preferred to be made of postcard paper or triplex paper. However, optionally the removable gravity-operated angular indicator 180 of airway evaluator 100 may be a reusable component, which can be detached from plate 150 and attached to a new plate 150. For multiple uses, the materials of all components of the device are suitable for sterilization.

In a further aspect, the present invention provides a method of evaluation of airway for orotracheal intubation using the multifunctional airway evaluator described above. More specifically, the multifunctional airway evaluator of the present invention can be used for multiple distance and angular measurements involved in airway evaluation. These include, but not limited to, measurements of mouth opening distance, thyromental distance, mandibular angle distance, mandibulohyoid distance, and neck mobility.

Mouth opening distance is defined as the distance between mandibular and maxillary central incisors measured while a patient's mouth is fully opened. However, there are three types of patients according to teeth distribution in the mouth, and the mouth opening distance is measured according to the patient type. For a patient with complete dental arch, mouth opening distance is measured as the distance between the incisors teeth. For a patient with incomplete teeth, mouth opening distance is measured as if they present complete dental arch. For a patient without teeth, mouth opening distance is measured as the distance between the upper and lower gingivae. It has been found that mouth opening distance indicates movement of the temporomandibular joint and that significantly limited mouth opening hinders exposure of the larynx. Typically, a mouth opening distance of 4 cm or more is considered normal. A threshold distance of 4 cm for mouth opening distance can be indicated in the distance scale 60 of airway evaluator 10 or 100, as illustrated in FIG. 6.

Thyromental distance is defined as the distance between the bone point of the mentum of the mandible and the thyroid notch while the patient's neck is fully extended. This measurement helps in determining how readily the laryngeal axis will fall in line with the pharyngeal axis when the atlanto-occipital joint is extended. Alignment of these two axes is difficult if the thyromental distance is <6 cm in adults, or <3 finger breadths as traditionally stated; 6-6.5 cm is less difficult, while >6.5 cm is considered normal. A threshold distance of 6 cm for thyromental distance can be indicated in the distance scale 60 of airway evaluator 10 or 100, as illustrated in FIG. 6.

Mandibular angle distance is defined as the distance between the left and the right mandibular angles. Typically, a mandibular angle distance of 9 cm or more is considered normal. A threshold distance of 9 cm for mandibular angle distance can be indicated in the distance scale 60 of airway evaluator 10 or 100, as illustrated in FIG. 6.

The neck or cervical spine mobility is determined by a flexion angle between two positions, namely from the first position when a patient's head and cervical spine are in the vertical position, to the second position when the patient tilts his head upwardly to a maximum extent, while maintaining cervical spine in a neutral position. Typically, this flexion angle equal or higher than 35 degree is considered normal.

Figure 13:
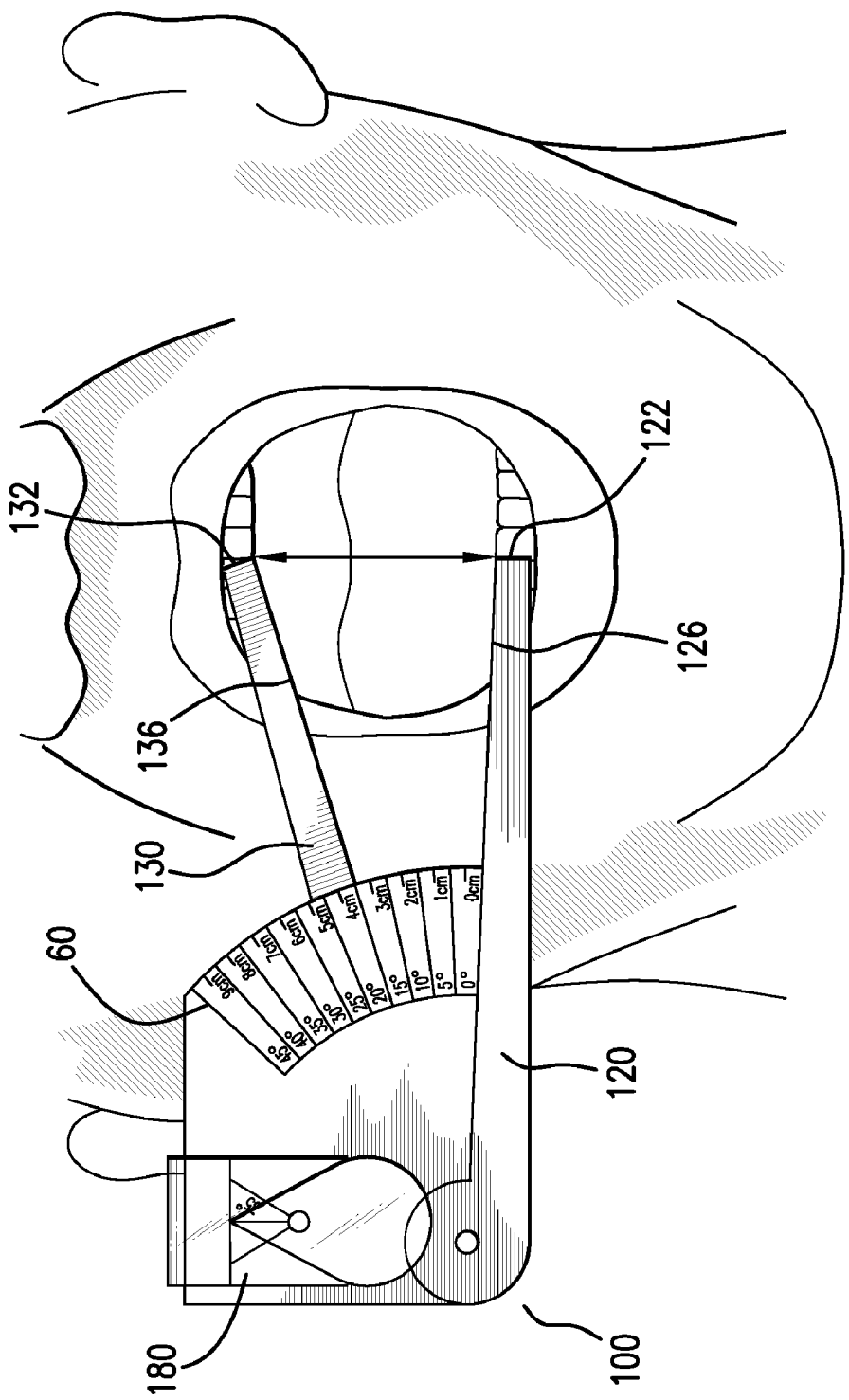
FIG. 13 is an illustrative view of a measurement of the mouth opening distance of a patient using the airway evaluator shown in FIG. 10.

FIG. 13 illustrates using multifunctional airway evaluator 100 described above to measure the mouth opening distance of a patient. The doctor adjusts the second arm 130 relative to first arm 120, and places distal ends 122 and 132 of the first and second arms against or next to the patient's mandibular and maxillary central incisors, respectively, while the patient's mouth is fully open. As shown, the inner edge 126 of first arm 120 is placed in line with the upper edge of the mandibular central incisors and the inner edge 136 of second arm 130 is placed in line with the lower edge of maxillary central incisors. Then, the distance between the inner edges 126 and 136 of the first and second arms at their distal ends is read on the distance scale 60. As described above, using the embodiment of the device shown, the measured mouth opening distance is read on the distance scale 60 at the position that the inner edge 136 of the second arm is in line with. The measured mouth opening distance is recorded in the patient's medical record.

Figure 14:
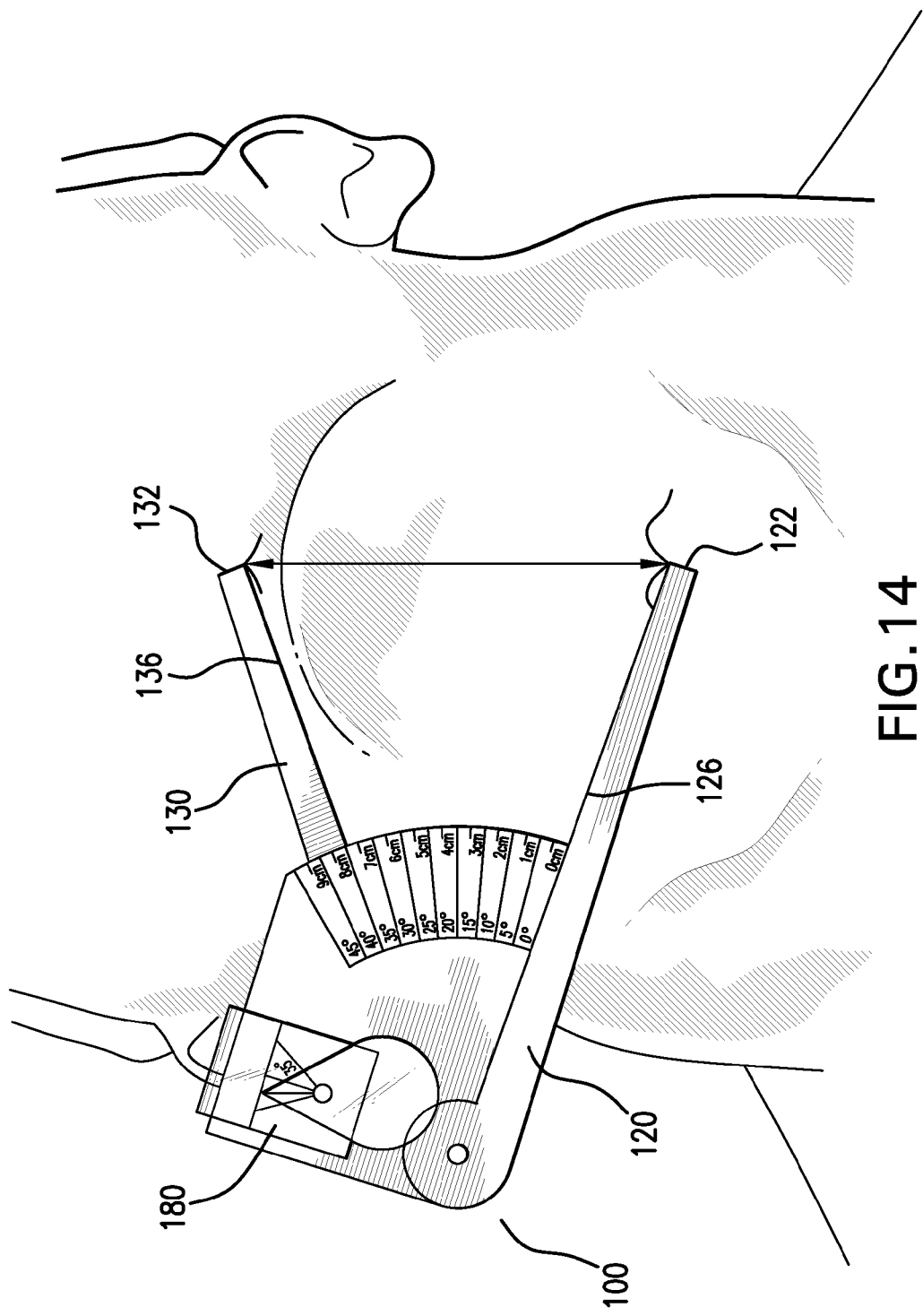
FIG. 14 is an illustrative view of a measurement of the thyromental distance of a patient using the airway evaluator shown in FIG. 10.

FIG. 14 illustrates measurement of the thyromental distance of the patient using multifunctional airway evaluator 100. Typically, the doctor makes markers first at the patient's bone point of the mentum of the mandible and thyroid notch, respectively, according to conventional medical examination procedure. The doctor adjusts the second arm 130 relative to first arm 120, and places distal ends 122 and 132 of the first and second arms against or next to the patient's thyroid notch and bone point of the mentum of the mandible, respectively, while the neck of said patient is in full extension. As shown, the inner edge 126 of first arm 120 is placed in line with the marker of the thyroid notch and the inner edge 136 of second arm 130 is placed in line with the marker of the bone point of the mentum of the mandible. Then, the distance between the distal ends of the first and second arms is read on the distance scale 60 to obtain the measured thyromental distance, as described above in detail in reference to mouth opening distance measurement. The measured thyromental distance is recorded in the patient's medical record.

Figure 15:
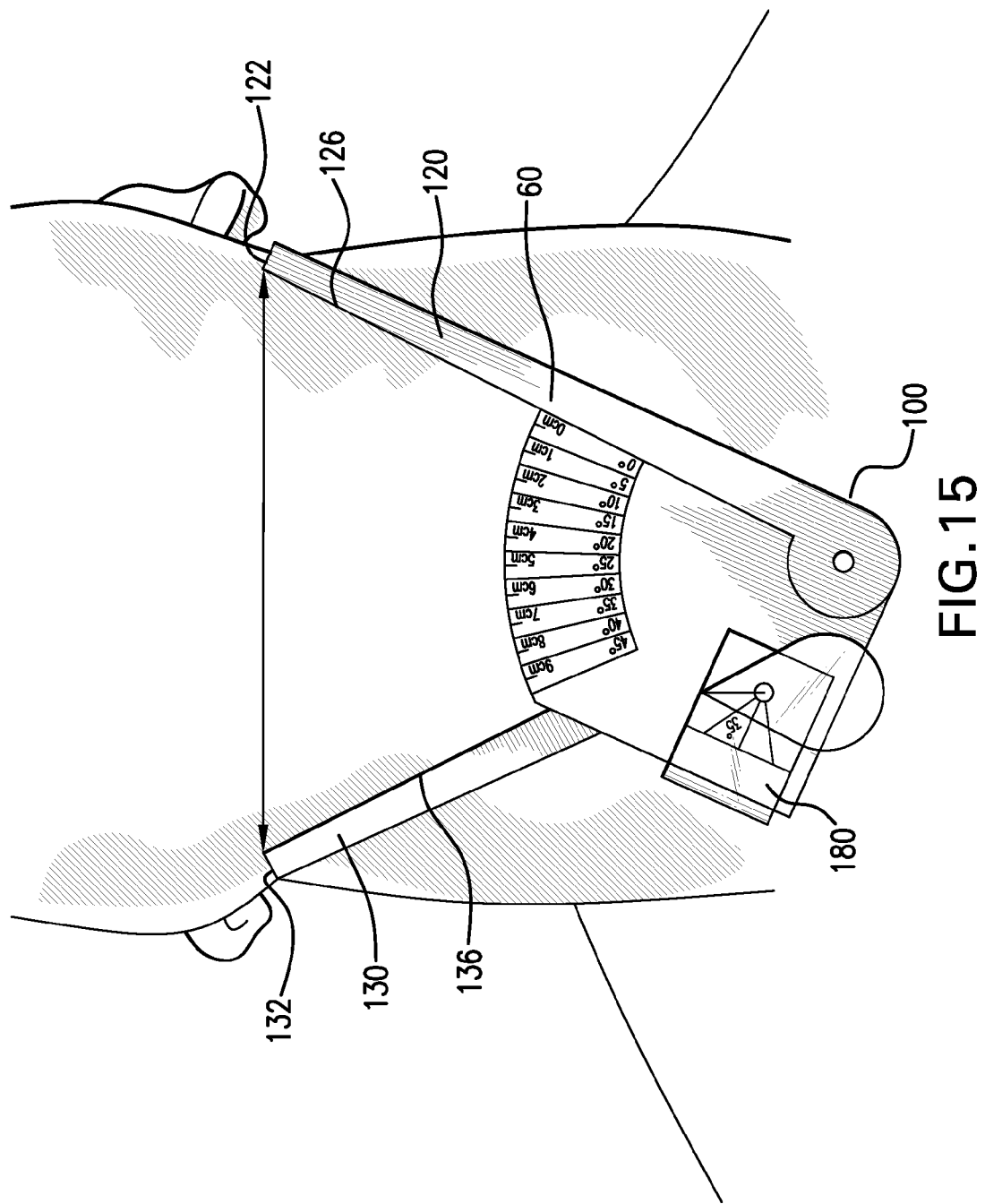
FIG. 15 is an illustrative view of a measurement of the mandibular angle distance of a patient using the airway evaluator shown in FIG. 10.

FIG. 15 further illustrates measurement of the mandibular angle distance of the patient using multifunctional airway evaluator 100. As shown, distal ends 122 and 132 of the first and second arms are placed against the left mandibular angle and the right mandibular angle of the patient, respectively. Then, the distance between the distal ends of the first and second arms is read on the distance scale 60 to obtain the measured mandibular angle distance, as described above in detail in reference to mouth opening distance measurement. The measured mandibular angle distance is recorded in the patient's medical record.

Figure 16A:
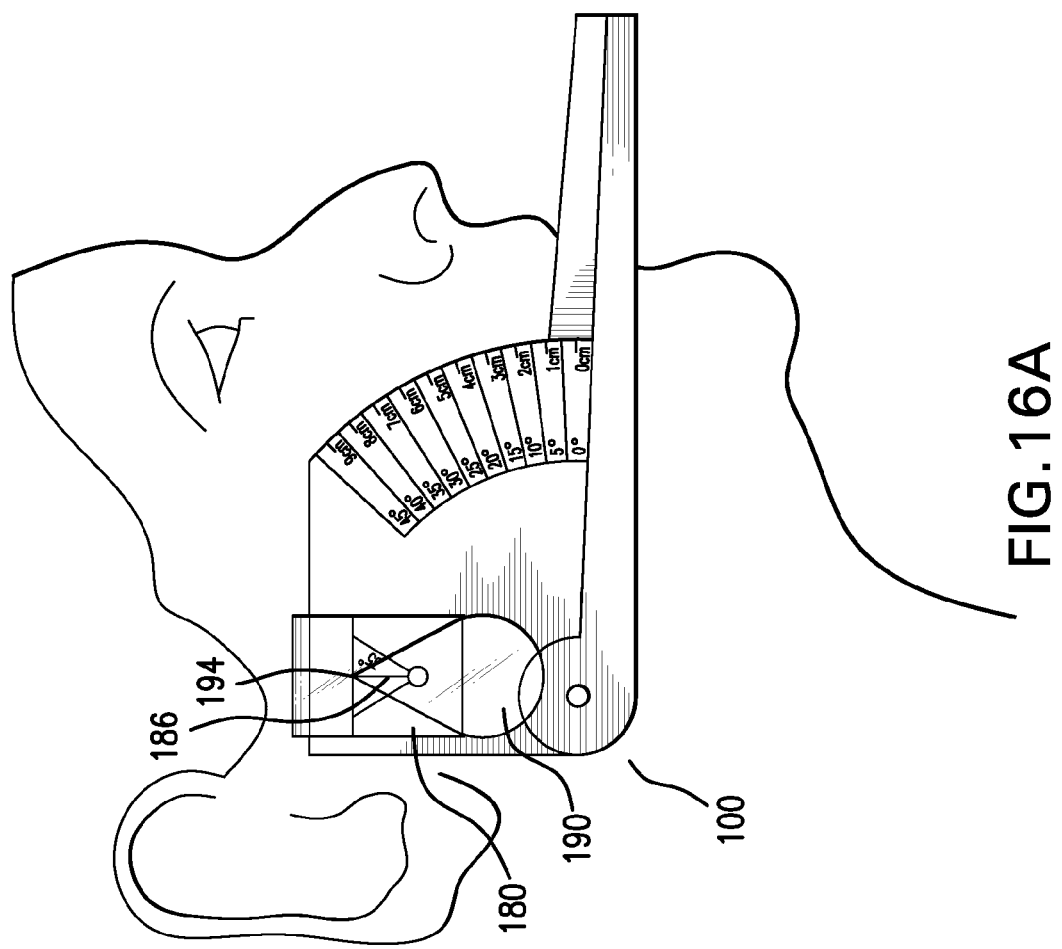
FIGS. 16A and 16B are illustrative views of a measurement of the neck mobility of a patient using the airway evaluator shown in FIG. 10.
Figure 16B:
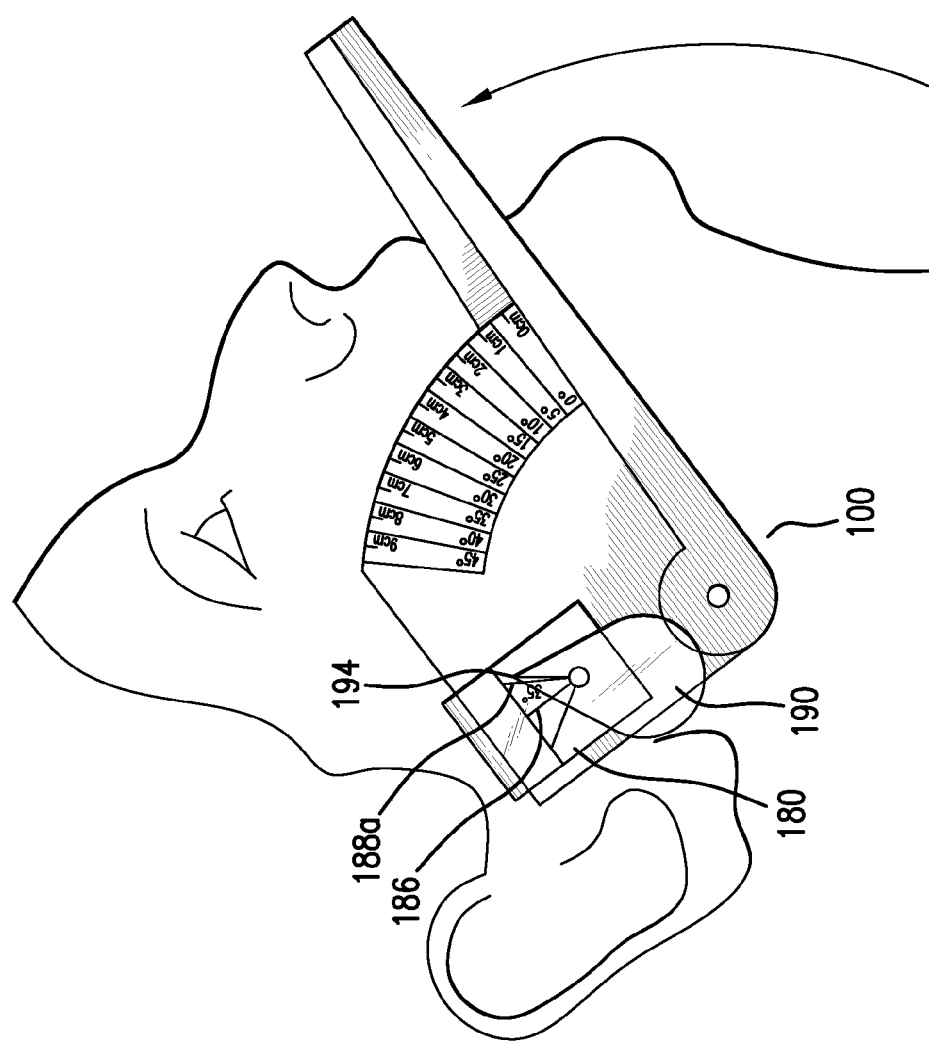

FIGS. 16A and 16B illustrate the measurement of the neck mobility of the patient using multifunctional airway evaluator 100. As shown in FIG. 16A, planar plate 150 is first fixed at the pre-auricular area of the patient, either by a double-sided tape, or by a finger pressing against the patient's face to hold plate 150 stationary. When plate 150 is fixed, the zero-degree reference line 186 of gravity-operated angular indicator 180 is positioned vertically. As shown, at this time the pointed upper end 194 of rotating disk 190 is aligned with zero-degree reference line 186. Then, the patient is instructed to lift up his chin to tilt his head upwardly to a maximum extent while maintaining the cervical spine in a neutral position.

As shown in FIG. 16B, when the patient's head tilts upwardly, the plate 150 is tilted from its original position shown in FIG. 16A. However, at the same time rotating disk 190 rotates around axial pin 182, and stays at the vertical position. Now, the pointed upper end 194 of rotating disk 190 points beyond assessment line 188*a*. It is noted that using airway evaluator 100, the neck mobility is judged by the extent of rotation equal or higher than the predetermined threshold angle (beyond assessment line 188*a*), or less than the predetermined threshold angle (within assessment line 188*a*). In the example shown in FIG. 16B, the patient's neck mobility is higher than the threshold angle of 35 degrees. The extent of rotation, in other words the measured neck mobility, is recorded in the patient's medical record.

In FIGS. 16A and 16B, airway evaluator 100 is placed on the right side of the patient's face. However, if for any reason it is not feasible to attach the device to the right side of the patient's face, gravity-operated angular indicator 180 can be detached, reversed, and fastened on plate 150 with the rotating disk 190 disposed on the rear side of plate 150. Then, plate 150 can be placed on the left side of the patient's face to measure neck mobility as described above.

As can be appreciated, the multifunctional airway evaluator of the present invention has several advantages. The multifunctional airway evaluator provides a measurement device that enables doctors or other medical professionals to accurately evaluate airway for orotracheal intubation. This overcomes the difficulties involved in making the required measurement without appropriate equipment, and reduces errors introduced by improper measurements. Accurate airway evaluation and preoperative prediction of potential difficulty with intubation can help reduce the incidence of catastrophic complications by alerting doctors to take additional precautions before beginning anesthesia or other procedures.

As described above, all measured parameters are recorded in the patient's medical record, which can be easily maintained in an electronic medical record and made readily accessible to doctors. The availability of an objective, easily documented, reproducible airway evaluation result in the medical record ultimately improves quality of medical care. For example, if the airway evaluation result in the medical record indicates a difficult intubation, a resident, fellow, certified registered nurse anesthetist, or junior doctor can request the presence and/or assistance of a senior doctor during the procedure. On the other hand, if the evaluation result predicts a normal intubation while a difficult intubation occurs, the medical record will assist in any subsequent risk management or resolving medicolegal issues.

The airway evaluator of the present invention is an integrated multifunctional device that integrates two different measurement mechanisms into one portable device. This allows all distance and angular measurements for airway evaluation for orotracheal intubation to be performed using one single device. Moreover, the removable feature of gravity-operated angular indicator 180 of airway evaluator 100 provides further flexibility of the device in clinical use. The multifunctional airway evaluator is small and portable, and it can be conveniently carried around by doctors in their pockets, or provided at various locations in hospitals or medical facilities where the subject measurements may be performed. The multifunctional airway evaluator can be manufactured with very low cost, and thus is particularly suitable for mass production for a disposable device.

As can be appreciated, the utilities and advantages of the multifunctional airway evaluator of the present invention have met a strong need in airway evaluation and in improvement of the quality of medical care.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

What is claimed is:

1. A multifunctional airway evaluator for orotracheal intubation comprising:
   (a) a first elongated arm having a distal end and an opposing hinge end;
   (b) a second elongated arm having a distal end and an opposing hinge end connected to said hinge end of said first arm by a pivot connection; said first and second arms movable relative to each other about a pivotal axis of said pivot connection;
   (c) a planar plate connected to said first arm, extending upwardly from said first arm between said hinge end and a middle portion of said first arm, said planar plate including a distance scale on a front face thereof, disposed along a side edge of said plate at said middle portion of said first arm, toward said distal ends of said arms; said distance scale including a plurality of spaced apart grade lines aligned radially with said pivotal axis and distance parameters associated therewith, wherein when said second arm is rotated to a position relative to said first arm for measurement, one of said grade lines of said distance scale aligned with said second arm indicates a measured distance between said distal ends of said first and second arms at said position; and
   (d) a gravity-operated angular indicator attached to said planar plate, said gravity-operated angular indicator including an axial pin disposed perpendicular to said planar plate, a rotating disk pivotally attached to and rotatable around said axial pin by gravity, and one or more angular measurement marker affixed adjacent said rotating disk.

2. The airway evaluator of claim 1, wherein an inner edge of said second arm and an inner edge of said first arm are aligned with said pivotal axis, and said measured distance between said first and second arms at said position is a distance between said inner edges of said first and second arms at said distal ends thereof.

3. The airway evaluator of claim 1, wherein said pivot axis is in alignment with central axes of said first and second arms, and said measured distance between said first and second arms at said position is a distance between said central axes of said first and second arms at said distal ends thereof.

4. The airway evaluator of claim 1, wherein said first and second arms are linear and have a same length.

5. The airway evaluator of claim 1, wherein said planar plate and said first arm are made of one integral piece of a material.

6. The airway evaluator of claim 1, wherein said side edge of said planar plate at said middle portion of said first arm is circularly curved, and said distance scale is disposed along said circularly curved side edge.

7. The airway evaluator of claim 1, wherein said distance parameters of said distance scale are in metric or English units.

8. The airway evaluator of claim 1, wherein said distance scale further includes one or more threshold marker, indicating one or more predetermined threshold distance.

9. The airway evaluator of claim 1, wherein said planar plate further includes an angular scale aside said distance scale.

10. The airway evaluator of claim 1, wherein said rotating disk of said gravity-operated angular indicator has a mass center distanced from said axial pin.

11. The airway evaluator of claim 10, wherein said rotating disk is attached to said axial pin at one third of a length of said rotating disk from an upper end thereof, along a vertical central axis of said rotating disk.

12. The airway evaluator of claim 1, wherein a plane of said rotating disk is in parallel with said planar plate.

13. The airway evaluator of claim 1, wherein said rotating disk has a pointed upper end.

14. The airway evaluator of claim 1, wherein said angular measurement marker includes a zero-degree reference line adapted to indicate a starting position of a rotational movement of said rotating disk.

15. The airway evaluator of claim 14, wherein said angular measurement marker of said gravity-operated angular indicator includes one or more assessment line aligned radially with said axial pin, representing at least one predetermined threshold angle, and one or more angular parameter associated with said threshold angle.

16. The airway evaluator of claim 1, wherein said axial pin of said gravity-operated angular indicator is attached to said planar plate.

17. The airway evaluator of claim 1, wherein said angular measurement marker of said gravity-operated angular indicator is provided on said front face of said planar plate.

18. The airway evaluator of claim 1, wherein said gravity-operated angular indicator further includes a base fastened to said planar plate, said axial pin and said rotating disk are attached to said base, and said angular measurement marker is placed on a front surface of said base.

19. The airway evaluator of claim 18, wherein said base has a shape of a clip and is slid onto an upper portion of said planar plate.

\* \* \* \* \*